Figure 1:
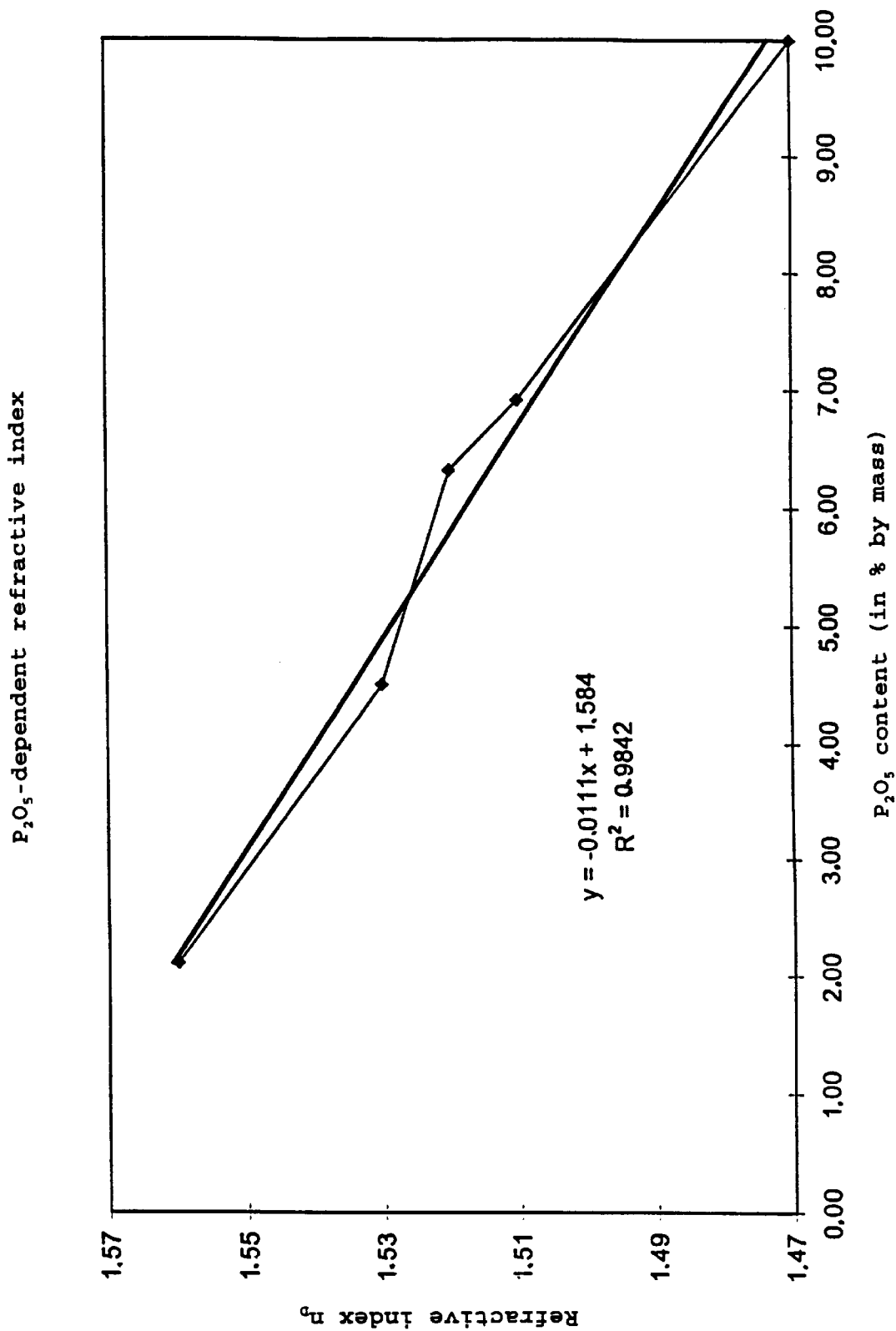

United States Patent [19]

Lück et al.

[11] Patent Number: 6,107,229
[45] Date of Patent: Aug. 22, 2000

[54] ALUMINOFLUOROSILICATE GLASS

[75] Inventors: Rainer Lück, Tornesch; Dieter Reif, Suhl; Barbara Leuner, Ilmenau, all of Germany

[73] Assignee: Ernst Mühlbauer KG, Germany

[21] Appl. No.: 09/100,071

[22] Filed: Jun. 19, 1998

[30] Foreign Application Priority Data

Jun. 19, 1997 [DE] Germany ............ 197 26 103

[51] Int. Cl.$^7$ ........................ A61K 6/02
[52] U.S. Cl. ............ 501/151; 501/30; 501/73; 106/35; 523/116; 523/117; 524/443; 524/556
[58] Field of Search .................. 523/116, 117; 524/556, 443; 501/151, 73, 30; 106/35

[56] References Cited

U.S. PATENT DOCUMENTS

| 4,192,795 | 3/1980 | Madhavan et al. ............ 523/116 |
| 4,629,746 | 12/1986 | Michl et al. . |
| 4,814,362 | 3/1989 | Billington et al. . |
| 5,051,453 | 9/1991 | Okabayashi et al. ............ 523/116 |
| 5,318,929 | 6/1994 | Jana et al. ............ 501/73 |
| 5,360,770 | 11/1994 | Chadwick . |

FOREIGN PATENT DOCUMENTS

| 0244959 | 9/1992 | European Pat. Off. . |
| 0219058 | 10/1994 | European Pat. Off. . |
| 0475239 | 1/1995 | European Pat. Off. . |
| 0132332 | 9/1978 | Germany ............ 501/73 |
| 132-332 | 9/1978 | Germany . |
| 3804469 | 8/1988 | Germany . |
| 60-239341 | 11/1985 | Japan ............ 501/73 |
| 60239341 | 11/1985 | Japan . |
| WO 86/00021 | 1/1986 | WIPO . |
| WO 88/05651 | 8/1988 | WIPO . |
| WO 93/17653 | 9/1993 | WIPO . |

*Primary Examiner*—Andrew E. C. Merriam
*Attorney, Agent, or Firm*—Medlen & Carroll, LLP

[57] ABSTRACT

The invention relates to an aluminofluorosilicate glass for use in a material for dental restoration, which has the following features:

a) a ratio of Al (calculated as $Al_2O_3$) to Si (calculated as $SiO_2$) of 0.57–1.12 by mass;

b) a total content of Mg (calculated as MgO) and Ba (calculated as BaO) of 29–36% by mass;

c) a ratio of Mg (calculated as MgO) to Ba (calculated as BaO) of 0.028–0.32 by mass;

d) a content of P (calculated as $P_2O_5$) of 2–10% by mass.

The glass according to the invention has a high radiopacity, and the refractive index $n_D$ for visible light can be adjusted by varying the phosphorus content.

8 Claims, 1 Drawing Sheet

ALUMINOFLUOROSILICATE GLASS

The present invention relates to a glass composition, namely an aluminofluorosilicate glass, which is suitable as component of dental restoration material. Aluminofluorosilicate glasses as component of materials for dental restoration are known. They are used, in particular, in glass ionomer cements (defined in ISO 7484) and in polymerizable cements as described in EP-A-0 219 058 and known under the name "compomer" and "plastic-reinforced glass ionomer cement" (Quintessenz 47, 1581 (1996)).

Dental materials of this type, in particular glass ionomer cements, are frequently transparent to X-rays. In the absence of X-ray contrast, radiographic examination of a tooth restored with such a cement is then impossible.

It has already been proposed in the prior art to confer radiopacity on dental cements. One method is to admix inorganic radiopaque fillers which contain, for example, higher alkaline earth metal oxides and/or rare earth metal oxides (DE-A 30 39 664, WO-A 86/00021, U.S. Pat. No. 4,629,746). In the case of glass ionomer cements it has been proposed additionally to add a radiopaque, inorganic filler material, for example strontium fluoride, to the polyalkenoate component and glass component (WO-A 88/05651, EP-A 244 959).

The prior art has also dealt with the development of aluminofluorosilicate glasses which are themselves radiopaque (U.S. Pat. Nos. 4,814,362, 5,360,770, WO-A 93/17653, DE-A 38 04 469, EP-A 475 239).

A dental material ought, apart from a certain radiopacity, also have a desired translucency for visible light. It is important in this connection that the refractive indices of the various components of the dental mixture are mutually harmonised.

The prior art has already dealt with, in the EP-A 475 239 which has already been mentioned, adjustment both of the refractive index and of the radiopacity of the glass. However, this publication describes a dental cement which has a complex composition and whose refractive index can be adjusted only within narrow limits.

The present invention is based on the object of providing a radiopaque aluminofluorosilicate glass whose refractive index nD for visible light can be adjusted in a simple manner and can thus be adapted to the refractive index of the polymer system used in the dental mixture.

This object is achieved by an aluminofluorosilicate glass which is characterized by the following features:

a) a ratio of Al (calculated as $Al_2O_3$) to Si (calculated as $SiO_2$) of 0.57–1.12 by mass;

b) a total content of Mg (calculated as MgO) and Ba (calculated as BaO) of 29–36% by mass;

c) a ratio of Mg (calculated as MgO) to Ba (calculated as BaO) of 0.028–0.32 by mass;

d) a content of P (calculated as $P_2O_5$) of 2–10% by mass.

The glass according to the invention acquires radiopacity in particular through the barium oxide content. For the purpose of the invention, the term "radiopaque" indicates an opacity corresponding at least to that of aluminium. A 1 mm-thick layer of the glass according to the invention thus has at least the same radiopacity as a 1 mm-thick aluminium layer.

The refractive index $n_D$ can in the case of the glass according to the invention surprisingly be adjusted in a specific manner by varying the phosphorus content calculated as $P_2O_5$. In the case of the glass according to the invention, a change in the contents of the other components of the glass has, by comparison, only a significantly smaller effect on the refractive index of the glass.

In the case of the glass according to the invention, the refractive index can be expressed as a function of the $P_2O_5$ content by the following empirically derived linear equation:

$$n_D = -0.0111(P_2O_5 \text{ in } \% \text{ by mass}) + 1.584$$

A BRIEF DESCRIPTION OF THE DRAWINGS

This linear equation makes it possible to calculate, with a coefficient of determination of 98%, the refractive index as a function of the $P_2O_5$ content (see also FIG. 1).

Thus, in the case of the glass according to the invention, the refractive index can be controlled through the $P_2O_5$ content, and the radiopacity can be varied by changing the composition of the glass in other ways, in particular by varying the barium oxide content within the scope prescribed according to the invention.

The glass according to the invention advantageously has a fluoride content of 7–14% by mass. It is likewise preferred for the sodium content to be 0.5–5% by mass (calculated as disodium oxide).

The glass preferably contains the following components (in % by mass);

| Al | (calculated as $Al_2O_3$) | 20–28 |
|---|---|---|
| Si | (calculated as $SiO_2$) | 25–35 |
| Ba | (calculated as BaO) | 25–35 |
| Mg | (calculated as MgO) | 1–8 |
| Na | (calculated as $Na_2O$) | 0.5–5 |
| F | | 7–14 |

The list of these components is not definitive; other components (for example other alkali metals or alkaline earth metals and/or rare earth metals) and impurities may be present.

The production of an aluminofluorosilicate glass according to the invention takes place in a known manner by fusion from the (preferably analytically pure) starting materials which may contain the metals to be employed for example as oxides, fluorides and/or phosphates. After a homogeneous melt has been obtained, it is dragaded in distilled water and comminuted, in particular ground, to the required particle size. Particles sizes preferred for use in dental cements are those having an average particle size below 10 $\mu$m, for example about 4 $\mu$m, or else around 1 $\mu$m.

The aluminofluorosilicate glass according to the invention can be used as component of a dental material for prosthetic, conservative and/or preventive dental treatment.

The glass according to the invention is particularly suitable as component of a radiopaque polymerizable cement. It is possible by adding the aluminofluorosilicate glass according to the invention to produce polymerizable cements which, because of the possibility of adapting the refractive index of the glass component to that of the polymer system used, have good translucency. The radiopacity of this material can be in the range 200–300%, that is to say a 1 mm-thick layer of the polymerizable cement has the same radiopacity as a 2–3 mm-thick aluminium layer.

The glass according to the invention can furthermore be used for producing a glass ionomer cement complying with ISO 7484.

In the drawing, FIG. 1 shows a graph of the dependence of the refractive index on the $P_2O_5$ content of the glass. An empirical line has been drawn through the measurement points, and the linear equation for this has already been mentioned above.

Exemplary embodiments of the invention are explained below.

EXAMPLE 1
Production of Aluminofluorosilicate Glasses According to the Invention.

Ground quartz, aluminium hydroxide, aluminium fluoride, aluminium phosphate, cryolite, barium fluoride and magnesium carbonate are fused in a platinum crucible at 1400° C. The amounts of the starting materials employed are chosen in each exemplary embodiment so that the resulting glasses have the compositions evident from the following table. Heating is continued until a clear, homogeneous and residue-free melt is obtained. The low-viscosity melt is dragaded in distilled water. The resulting glass granules are dried and made available in this form for further processing as component of dental materials. The refractive index $n_D$ of the resulting glasses is likewise evident from the table.

| Component (% by mass) | Glass No. 1 | Glass No. 2 | Glass No. 4 | Glass No. 5 | Glass No. 6 |
|---|---|---|---|---|---|
| $Al_2O_3$ | 20.1 | 26.0 | 26.1 | 27.2 | 23.2 |
| $SiO_2$ | 35.0 | 25.1 | 27.0 | 25.0 | 29.3 |
| BaO | 34.9 | 25.0 | 28.7 | 27.2 | 29.4 |
| $P_2O_5$ | 4.5 | 6.9 | 2.1 | 10.0 | 6.3 |
| $Na_2O$ | 0.5 | 5.0 | 2.9 | 2.8 | 1.5 |
| MgO | 1.1 | 7.9 | 5.1 | 2.1 | 4.9 |
| F | 6.9 | 7.1 | 14.0 | 9.9 | 9.3 |
| Refractive index $n_D$ | 1.53 | 1.51 | 1.56 | 1.47 | 1.52 |

EXAMPLE 2
Production of a Polymerizable Dental Cement.

The dragaded glass obtained as glass No. 5 according to the above table is ground to an average particle size of 4 μm. 30 g of glass powder are mixed with 7 g of urethane dimethacrylate, 5 g of succinic acid monomethacrylic acid ester, 5 g of hexanediol dimethacrylate, 1 g of Aerosil® R972 (supplied by Degussa), and 90 mg of camphorquinone and 130 mg of dimethylaminobenzoic acid as starter.

A test specimen with a layer thickness of 1 mm and a diameter of 2 cm is shaped from the resulting mixture, and this test specimen is irradiated with a Dentacolor XS lamp for 90 s. The cured material has a radiopacity of 200% and an opacity for visible light of 18%.

What is claimed is:

1. An aluminofluorosilicate glass, comprising aluminum, silicon, magnesium, barium, fluoride, and phosphorus, wherein the ratio by mass of said aluminum calculated as $Al_2O_3$ to said silicon calculated as $SiO_2$ is within the range of 0.57–1.12, wherein the ratio by mass of said magnesium calculated as MgO to said barium calculated as BaO is within the range of 0.028–0.32, wherein the total content by mass of said magnesium calculated as MgO and said barium calculated as BaO is within the range of 29–36%, wherein said phosphorus calculated as $P_2O_5$ is about 2–10% by mass, and wherein said fluoride is about 7–14% by mass.

2. The aluminofluorosilicate glass of claim 1, further comprising about 0.5–5% by mass of sodium calculated as $Na_2O$.

3. An aluminofluorosilicate glass comprising about 20–28 weight % aluminum calculated as $Al_2O_3$, about 25–35 weight % silicon calculated as $SiO_2$, about 25–35 weight % barium calculated as BaO, about 1–8 weight % magnesium calculated as MgO, about 0.5–5 weight % sodium calculated as $Na_2O$, about 7–14 weight percent fluoride, and about 2–10% by mass phosphorus, wherein the total content of said magnesium calculated as MgO and said barium calculated as BaO is about 29–36 weight %, and wherein the ratio by mass of said magnesium calculated as MgO to said barium calculated as BaO is about 0.028–0.32.

4. A composition for use in producing a radiopaque dental material, comprising an aluminofluorosilicate glass, wherein said aluminofluorosilicate glass comprises aluminum, silicon, magnesium, barium, fluoride, and phosphorus, wherein the ratio by mass of said aluminum calculated as $Al_2O_3$ to said silicon calculated as $SiO_2$ is within the range of 0.57–1.12, wherein the ratio by mass of said magnesium calculated as MgO to said barium calculated as BaO is within the range of 0.028–0.32, wherein the total content by mass of said magnesium calculated as MgO and said barium calculated as BaO is within the range of 29–36%, wherein said phosphorus calculated as $P_2O_5$ is about 2–10% by mass, wherein said fluoride is about 7–14% by mass.

5. The composition of claim 4, wherein said aluminofluorosilicate glass further comprises about 0.5–5% by mass of sodium calculated as $Na_2O$.

6. A composition comprising an aluminofluorosilicate glass, wherein said aluminofluorosilicate glass comprises about 20–28 weight % aluminum calculated as $Al_2O_3$, about 25–35 weight % silicon calculated as $SiO_2$, about 25–35 weight % barium calculated as BaO, about 1–8 weight % magnesium calculated as MgO, about 0.5–5 weight % sodium calculated as $Na_2O$, about 7–14 weight percent fluoride, and about 2–10% by mass phosphorus, wherein the total content of said magnesium calculated as MgO and said barium calculated as BaO is about 29–36 weight %, and wherein the ratio by mass of said magnesium calculated as MgO to said barium calculated as BaO is about 0.028–0.32.

7. The composition of claim 6, wherein said dental material is selected from the group consisting of polymerizable dental cement and glass ionomer cement.

8. The composition of claim 6, wherein said aluminofluorosilicate glass is radiopaque.

* * * * *